US012686662B2

(12) United States Patent
He et al.

(10) Patent No.: US 12,686,662 B2
(45) Date of Patent: Jul. 21, 2026

(54) USE OF SILICON COMPOUNDS IN CYCLIZATION REACTIONS

(71) Applicants: Lanzhou Chemspec Technology Co., Ltd, Lanzhou (CN); Shanghai Chemspec Corporation, Shanghai (CN)

(72) Inventors: Li He, Shanghai (CN); Xiaoliang Li, Shanghai (CN); Zhenli Liu, Shanghai (CN); Zhong Tian, Shanghai (CN); Hanqing Duan, Shanghai (CN)

(73) Assignees: Lanzhou Chemspec Technology Co., Ltd., Lanzhou (CN); Shanghai Chemspec Corporation, Shanghai (CN)

( * ) Notice: Subject to any disclaimer, the term of this patent is extended or adjusted under 35 U.S.C. 154(b) by 345 days.

(21) Appl. No.: 18/275,612

(22) PCT Filed: Jan. 27, 2022

(86) PCT No.: PCT/CN2022/074346

§ 371 (c)(1),
(2) Date: Aug. 3, 2023

(87) PCT Pub. No.: WO2022/166764

PCT Pub. Date: Aug. 11, 2022

(65) Prior Publication Data

US 2024/0124401 A1 Apr. 18, 2024

(30) Foreign Application Priority Data

Feb. 7, 2021 (CN) ......................... 202110180140.1

(51) Int. Cl.
*C07D 213/61* (2006.01)
*B01J 31/02* (2006.01)
*C07D 271/10* (2006.01)

(52) U.S. Cl.
CPC ........ *C07D 213/61* (2013.01); *B01J 31/0247* (2013.01); *B01J 31/0274* (2013.01); *C07D 271/10* (2013.01); *B01J 2231/005* (2013.01); *B01J 2531/002* (2013.01)

(58) Field of Classification Search
CPC .. C07D 213/61; C07D 271/10; B01J 31/0247; B01J 31/0274; B01J 2231/005; B01J 2531/002
USPC ........................................................ 546/250
See application file for complete search history.

(56) References Cited

U.S. PATENT DOCUMENTS

| | | | |
|---|---|---|---|
| 4,245,098 | A | 1/1981 | Steiner et al. |
| 4,469,896 | A | 9/1984 | Steiner et al. |
| 4,665,186 | A | 5/1987 | Steiner et al. |
| 2013/0338196 | A1 | 12/2013 | Boger et al. |

FOREIGN PATENT DOCUMENTS

| | | | |
|---|---|---|---|
| CN | 101948424 | A | 1/2011 |
| CN | 103396357 | A | 11/2013 |
| CN | 106699647 | A | 5/2017 |
| JP | S61191663 | A | 8/1986 |
| WO | WO 2012048502 | A1 | 4/2012 |
| WO | 2012106569 | A | 8/2012 |
| WO | WO 2012106569 | A1 | 8/2012 |

OTHER PUBLICATIONS

Benoit Rigo et al., "Disilyltaed Compounds As Precursors Of Heterocycles: A New and Easy Oxadiazole Synthesis" Synthetic Communications, vol. 19, No. 13&14, Dec. 31, 1989, p. 2321-2335, USA.

*Primary Examiner* — Kristin A Vajda
(74) *Attorney, Agent, or Firm* — IPRTOP LLC

(57) ABSTRACT

A first aspect of the present invention provides a method for the preparation of 2-chloro-5-chloromethylpyridine, comprising: performing a cyclization reaction on 4,5-dichloro-4-methoxypentanenitrile in presence of a silicon compound and an acylamide compound to obtain 2-chloro-5-chloromethylpyridine. Another aspect of the present invention provides a method for preparation of 2-(chloromethyl)-5-(trifluoromethyl)-1,3,4-oxadiazole, comprising: performing a cyclization reaction on 1-(chloroacetyl)-2-(trifluoroacetyl) hydrazine in a presence of a silicon compound and an acylamide compound to obtain 2-(chloromethyl)-5-(trifluoromethyl)-1,3,4-oxadiazole. The silicon compound or/and acylamide compound provided by the present invention serve as cyclization reagents and have high efficiency.

14 Claims, No Drawings

USE OF SILICON COMPOUNDS IN CYCLIZATION REACTIONS

FIELD OF TECHNOLOGY

The present invention relates to the technical field of organic chemistry, in particular, to a use of silicon compounds in cyclization reactions.

BACKGROUND 2-chloro-5-chloromethylpyridine (CCMP) is an important intermediate for best-selling pesticides (e.g. imidacloprid, acetamiprid, thiacloprid, and nitenpyram) and the anticancer drug Abemaciclib (Bemaciclib, LY-2835219), which is also chemically known as N-[5-[(4-ethylpiperazin-1-yl)methyl] pyridin-2-yl]-5-fluoro-4-(7-fluoro-2-methyl-3-propan-2-yl-benzimidazol-5-yl)pyrimidin-2-amine. There are three main synthetic routes for 2-chloro-5-chloromethylpyridine, namely benzylamine method, cyclopentadiene method, and morpholine method. Most domestic manufacturers use the cyclopentadiene route, in which the reaction equation in the cyclization step is as follows:

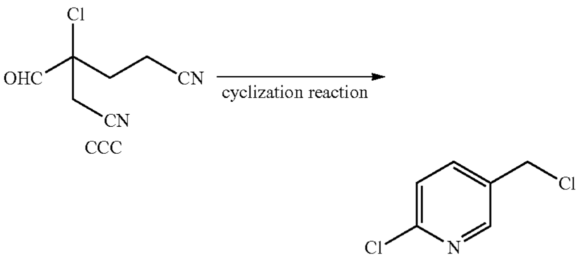

CCC

CCMP

The cyclization reagents used in this cyclization step are generally phosphorus oxychloride (Fine and Specialty Chemicals, 18(1), 47-49; 2010) or phosphorus pentachloride (U.S. Pat. No. 5,229,519), as well as triphosgene or phosgene. Phosphorus-containing reagents have higher cyclization yields and lower costs, but they produce large amounts of phosphorus-containing wastewater with a COD of about 150,000-200,000 ppm. With an annual production of nearly 10,000 tons of CCMP, 60,000 tons of phosphorus-containing wastewater will be generated. In addition, cycling with phosgene causes high toxicity and poor safety, so few companies use this reagent.

2-(chloromethyl)-5-(trifluoromethyl)-1,3,4-oxadiazole is one of the key intermediates of sitagliptin for the treatment of diabetes, and its annual demand is more than 200 tons. The reaction equation in the cyclization step is as follows, and the cyclization reagent is phosphorus oxychloride. The cyclization also suffers from the above mentioned problems and produces a large amount of phosphorus-containing wastewater; specifically, about 5 tons of phosphorus-containing wastewater will be produced from preparation of one ton of products. During the reaction process, pyrophosphoric acid agglomerates, making stirring difficult or impossible, which is detrimental to operations and results in low scale-up production yield.

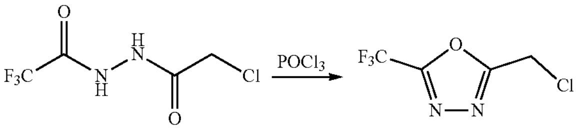

The discharge of phosphorus-containing wastewater, which can cause environmental hazards and eutrophication of water and damage the ecological balance, has been a major problem. It is difficult or expensive to bring the phosphorus-containing wastewater directly up to standard using existing technical means.

Therefore, it is urgent in this field to develop a low-cost and efficient cyclization method for 2-chloro-5-chloromethylpyridine and 2-(chloromethyl)-5-(trifluoromethyl)-1,3,4-oxadiazole, which allows by-products to be easily recovered, phosphorus-containing wastewater from the production process to be effectively decreased, and environmental hazards to be reduced.

SUMMARY

The present invention provides a use of silicone compounds in cyclization reactions for solving the problems of the prior art.

To achieve these and other related purposes, an aspect of the present invention provides a method for preparation of 2-chloro-5-chloromethylpyridine, comprising: performing a cyclization reaction on 4,5-dichloro-4-methoxypentanenitrile in presence of a silicon compound and an acylamide compound to obtain 2-chloro-5-chloromethylpyridine, where the reaction equation is as follows:

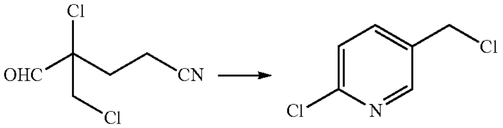

I II the silicon compound is selected from one or more of compounds having a chemical structural formula shown below:

V

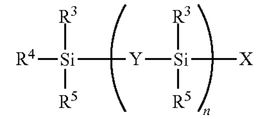

where $R^3$, $R^4$, and $R^5$ are each independently selected from H, Ph, C1-C4 alkyl, Cl, and Br;

Y is O or is not present;

n is selected from 0, 1, 2, 3, 4, and 5; and

X is selected from Cl and Br.

In some embodiments of the present invention, for the silicon compound having the chemical structural formula shown as V, each of $R^3$, $R^4$, and $R^5$ is independently selected from H, C1-C2 alkyl, Cl, and Br;

n is selected from 0 and 1; and X is selected from Cl and Br.

In some embodiments of the present invention, the silicon compound is selected from one or more of methyltrichlorosilane, dichlorodiethylsilane, dichlorodimethylsilane, trimethylchlorosilane, 1,1,2,2-tetrachloro-1,2-dimethyldisilane, silicon tetrachloride, dibromo(dimethyl)silane, bromotrimethylsilane, 1,3-dichloro-1,1,3,3-tetramethyldisiloxane.

In some embodiments of the present invention, the acylamide compound has a chemical structural formula shown as $RCONR^1R^2$, where R is selected from hydrogen, saturated or unsaturated C1 to C8 aliphatic groups, and substituted or unsubstituted phenyl, $R^1$ and $R^2$ are each independently selected from saturated or unsaturated C1 to C8 aliphatic groups and phenyl; or, R and $R^1$, or R and $R^2$ together with their attached atoms form a five- or six-membered heterocyclic group. Preferably, the acylamide compound is selected from one or more of N,N-dimethylformamide, N,N-diethylformamide, N,N-dimethylacetamide, N,N-diethylacetamide, N,N-diethylpropionamide, N,N-dimethylpropionamide, N,N-diphenylformamide, N,N-diphenylacetamide, N-methylpyrrolidone, and 1,3-dimethyl-2-imidazolidinone;

and/or, in the cyclization reaction, a molar ratio of the compound of formula I to the acylamide compound is 1: (0.1-1.5);

and/or, the cyclization reaction is carried out in the presence of a solvent, where the solvent is preferably a nonprotonic solvent, more preferably an aromatic hydrocarbon solvent;

and/or, the cyclization reaction is carried out at a temperature of 70 to 150° C.;

and/or, in the cyclization reaction, a molar ratio of the compound of formula I to the silicon compound is 1: (0.5-2.0);

and/or, a post-treatment of the cycloaddition reaction comprises: quenching with water, adjusting pH of the reaction system, performing solid-liquid separation, and removing the organic solvent.

In some embodiments of the present invention, the method further comprises: performing a reaction on a solid phase substance under an alkaline condition to obtain a silicon-oxygen compound, where the silicon-oxygen compound is preferably selected from silicates.

Another aspect of the present invention provides a method for preparation of 2-(chloromethyl)-5-(trifluoromethyl)-1,3,4-oxadiazole, comprising: performing a cyclization reaction on 1-(chloroacetyl)-2-(trifluoroacetyl)hydrazine in presence of a silicon compound and an acylamide compound to obtain 2-(chloromethyl)-5-(trifluoromethyl)-1,3,4-oxadiazole, where the reaction equation is as follows:

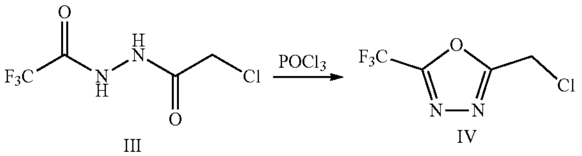

III IV the silicon compound is selected from one or more of compounds having a chemical structural formula shown below:

V

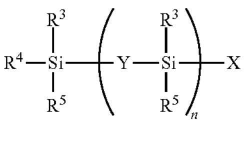

where $R^3$, $R^4$ and $R^5$ are each independently selected from H, Ph, C1-C4 alkyl, Cl, and Br;

Y is O or is not present;

n is selected from 0, 1, 2, 3, 4, and 5; and

X is selected from Cl and Br.

In some embodiments of the present invention, for the silicon compound having the chemical structural formula shown as V, each of $R^3$, $R^4$, and $R^5$ is independently selected from H, C1-C2 alkyl, Cl, and Br;

n is selected from 0 and 1; and

X is selected from Cl and Br.

In some embodiments of the present invention, the silicon compound is selected from one or more of methyltrichlorosilane, dichlorodiethylsilane, dichlorodimethylsilane, trimethylchlorosilane, 1,1,2,2-tetrachloro-1,2-dimethyldisilane, silicon tetrachloride, dibromo(dimethyl)silane, bromotrimethylsilane, 1,3-dichloro-1,1,3,3-tetramethyldisiloxane.

In some embodiments of the present invention, the acylamide compound has a chemical structural formula shown as $RCONR^1R^2$; R is selected from hydrogen, saturated or unsaturated C1 to C8 aliphatic groups, and substituted or unsubstituted phenyl; $R^1$ and $R^2$ are each independently selected from saturated or unsaturated C1 to C8 aliphatic groups and phenyl, or, R and $R^1$, or R and $R^2$ together with their attached atoms form a five- or six-membered heterocyclic group. Preferably, the acylamide compound is selected from one or more of N,N-dimethylformamide, N,N-diethylformamide, N,N-dimethylacetamide, N,N-diethylacetamide, N,N-diethylpropionamide, N,N-dimethylpropionamide, N,N-diphenylformamide, N,N-diphenylacetamide, N-methylpyrrolidone, and 1,3-dimethyl-2-imidazolidinone;

and/or, in the cyclization reaction, a molar ratio of the compound of formula III to the acylamide compound is 1: (0.1-1.5);

and/or, the cyclization reaction is carried out in the presence of a solvent, where the solvent is preferably a nonprotonic solvent, more preferably an aromatic hydrocarbon solvent;

and/or, the cyclization reaction is carried out at a temperature of 70 to 150° C.;

and/or, a molar ratio of the compound of formula III to the silicon compound is 1: (0.5-2.0);

and/or, a post-treatment of the cycloaddition reaction comprises: quenching with water, adjusting pH of the reaction system, performing solid-liquid separation, and removing the organic solvent.

In some embodiments of the present invention, the method further comprises: performing a reaction on a solid phase substance under an alkaline condition to obtain a silicon-oxygen compound, where the silicon-oxygen compound is preferably selected from silicates.

DETAILED DESCRIPTION

In order to make the purpose, technical solutions, and beneficial effects of the present invention clearer, the present invention is described in further detail below in conjunction with the embodiments, and those skilled in the art can easily understand other advantages and efficacy of the invention of this application as disclosed in the specification.

The inventors of the present invention have completed the present invention based on a lot of practical research and provide a new high-efficiency cyclization synthesis method by using silicon compounds or/and acylamide compounds as cyclization reagents, which has a higher comprehensive benefit relative to other methods in the prior art.

In this application, an "aliphatic group" usually refers to a group containing only carbon and hydrogen atoms, and is usually obtained after a corresponding hydrocarbon loses a hydrogen atom. The aliphatic group may be saturated or unsaturated, for example, alkyl, alkenyl, alkynyl, etc.

In this application, "alkyl" generally refers to saturated aliphatic groups, which may be straight chain or branch chain. For example, C1-C20 alkyl usually refers to an alkyl group including 1, 2, 3, 4, 5, 6, 7, 8, 9, 10, 11, 12, 13, 14, 15, 16, 17, 18, 19, or 20 carbon atoms. Alkyl groups include but are not limited to methyl, ethyl, propyl, isopropyl, butyl, n-butyl, isobutyl, sec-butyl, tert-butyl, pentyl, hexyl, heptyl, octyl, nonyl, decyl, undecyl, dodecanoyl, tridecyl, myristyl, pentadecyl, hexadecyl, heptadecyl, octadecyl, nonadecyl, eicosyl, etc.

In this application, "heterocyclic group" generally refers to a saturated or unsaturated (but not aromatic) cyclic hydrocarbon having at least one heteroatom selected from N, O, and S. The heterocyclic group may be unsubstituted or substituted, and may be five-membered or six-membered.

A first aspect of the present invention provides a method for the preparation of 2-chloro-5-chloromethylpyridine, comprising: performing a cyclization reaction on 4,5-dichloro-4-methoxypentanenitrile in presence of a silicon compound and an acylamide compound to obtain 2-chloro-5-chloromethylpyridine, where the reaction equation is as follows:

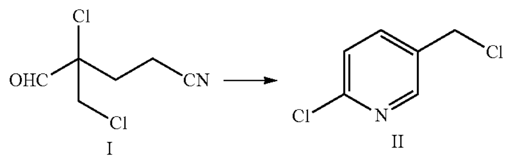

the silicon compound is selected from one or more of compounds having a chemical structural formula shown below:

V

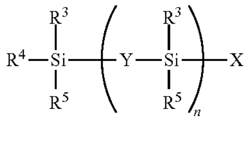

where $R^3$, $R^4$ and $R^5$ are each independently selected from H, Ph, C1-C4 alkyl, Cl, and Br, Y is O or is not present, n is selected from 0, 1, 2, 3, 4, and 5, and X is selected from Cl and Br.

In some embodiments of the present invention, for the silicon compound of formula V, each of $R^3$, $R^4$, and $R^5$ is independently selected from H, C1-C2 alkyl, Cl, and Br.

In another embodiment of the present invention, for the silicon compound of formula V, n is selected from 0 and 1.

In another embodiment of the present invention, for the silicon compound of formula V, X is selected from Cl and Br.

In another embodiment of the present invention, the silicon compound is selected from one or more of methyltrichlorosilane, dichlorodiethylsilane, dichlorodimethylsilane, trimethylchlorosilane, 1,1,2,2-tetrachloro-1,2-dimethyldisilane, silicon tetrachloride, dibromo(dimethyl)silane, bromotrimethylsilane, and 1,3-dichloro-1,1,3,3-tetramethyldisiloxane.

In the above cyclization reaction, the amount of silicon compound can be suitably adjusted with respect to the compound of formula I, so as to ensure the conversion rate of the reaction and to enable the reaction to be carried out in a sufficiently positive direction. For example, in the above-mentioned cyclization reaction, the molar ratio of the compound of formula I to the silicon compound may be 1:(0.5-2.0), 1:(0.5-0.6), 1:(0.6-0.7), 1:(0.7-0.8), 1: (0.8-0.9), 1:(0.9-1.0), 1: (1.0-1.1), 1:(1.1-1.2), 1: (1.2-1.3), 1:(1.3-1.4), 1:(1.4-1.5), 1:(1.5-1.6), 1:(1.6-1.7), 1: (1.7-1.8), 1: (1.8-1.9), or 1:(1.9-2.0).

In the above cyclization reaction, the acylamide compound usually serves as a cyclization reagent and has a chemical structural formula of $RCONR^1R^2$, where R is selected from hydrogen, saturated or unsaturated C1 to C8 aliphatic groups, and substituted or unsubstituted phenyl, $R^1$ and $R^2$ are each independently selected from saturated or unsaturated C1 to C8 aliphatic groups and phenyl, or, R and $R^1$, or R and $R^2$ together with their attached atoms form a five- or six-membered heterocyclic group. For instance, the acylamide compound is selected from one or more of N,N-dimethylformamide, N,N-diethylformamide, N,N-dimethylacetamide, N,N-diethylacetamide, N,N-diethylpropionamide, N,N-dimethylpropionamide, N,N-diphenylformamide, N,N-diphenylacetamide, N-methylpyrrolidone, and 1,3-dimethyl-2-imidazolidinone. In the above cyclization reaction, the amount of the acylamide compound can be suitably adjusted with respect to the compound of formula I, so as to ensure the conversion rate of the reaction and to enable the reaction to be carried out in a sufficiently positive direction. In the above cyclization reaction, a molar ratio of the compound of formula I to the acylamide compound may be 1: (0.1-1.5), 1:(0.1-0.2), 1:(0.2-0.3), 1:(0.3-0.4), 1:(0.4-0.5), 1:(0.5-0.6), 1:(0.6-0.7), 1:(0.7-0.8), 1:(0.8-0.9), 1:(0.9-1.0), 1:(1.0-1.1), 1:(1.1-1.2), 1:(1.2-1.3), 1:(1.3-1.4), or 1:(1.4-1.5).

The above cyclization reaction is usually carried out in the presence of a solvent, and the solvent is usually a nonprotonic solvent and may be conducive to the reaction system. The type and amount of suitable solvents may be suitably adjusted by those skilled in the art. For example, in the above-mentioned cyclization reaction, the solvent may be selected from aromatic hydrocarbon solvents, etc. In an embodiment of the present invention, the solvent in the above-mentioned cyclization reaction may be selected from one or more of benzene, toluene, dimethylbenzene, trimethylbenzene, chlorobenzene, dichlorobenzene, trichlorobenzene, etc. In an embodiment, in the above cyclization reaction, the weight of the solvent may be 1 to 8 times, 1 to 2 times, 2 to 4 times, or 4 to 8 times the weight of the reaction substrate.

In the above-mentioned cyclization reaction, the reaction may be carried out at a temperature ranging from room temperature to the boiling point of the solvent, and preferably under heated conditions. For example, in the above cyclization reaction, the temperature may be 70 to 150° C., 70 to 80° C., 80 to 90° C., 90 to 100° C., 100 to 110° C., 110 to 120° C., 120 to 130° C., 130 to 140° C., or 140 to 150° C. The person skilled in the art may adjust the reaction time according to the reaction process. For example, in the above-mentioned cyclization reaction, the reaction process may be determined by TLC, chromatography, and other methods. In an embodiment, in the above cyclization reaction, the reaction time may be 1 to 20 h, 1 to 2 h, 2 to 4 h, 4 to 6 h, 6 to 8 h, 8 to 12 h, or 12 to 20 h.

In the above cyclization reaction, the person skilled in the art may select a suitable method for the post-treatment of the reaction product, which may include, for example, quenching with water, adjusting pH of the system, performing solid-liquid separation, and removing organic solvent, so as to obtain 2-chloro-5-chloromethylpyridine. After the reaction, the system is quenched with water, the pH of the system is adjusted accordingly (e.g., adjusting the pH to be within a range from weakly acidic to weakly alkaline, more specifically it can be pH=6-8), the solid and liquid phases are separated, and the solvent is removed from the organic phase of the resulting liquid phase to yield 2-chloro-5-chloromethylpyridine. The obtained 2-chloro-5-chloromethylpyridine product may be further purified to provide 2-chloro-5-chloromethylpyridine with higher purity. Suitable purification methods (such as distillation) are known to those skilled in the art.

The method for preparation of 2-chloro-5-chloromethylpyridine provided by the present invention may further comprise: performing a reaction on the solid phase substance (obtained from the solid-liquid separation) under an alkaline condition to provide a silicon-oxygen compound. The above-mentioned solid phase substance includes mainly the silyl ether polymer produced during the cyclization reaction for the preparation of 2-chloro-5-chloromethylpyridine, which can be hydrolyzed into a corresponding silicon-oxygen compound under alkaline conditions.

In the above method for preparation of the silicon-oxygen compound, the silicon-oxygen compound varies depending on the substituents of the silicon compounds used in the cyclization reaction. For example, when $R^3$, $R^4$, and $R^5$ are each independently selected from Cl and Br, the resulting silicon-oxygen compound may be a silicate; when one of $R^3$, $R^4$, and $R^5$ is selected from Ph or C1-C4 alkyl and the remaining two are each independently selected from Cl and Br, the resulting silicon-oxygen compound may be a phenyl silicate or an alkyl silicate; when two of $R^3$, $R^4$, $R^5$ are each independently selected from C1-C4 alkyl and the remaining one is selected from Cl and Br, the resulting silicon-oxygen compound may be a polydialkylsiloxane; when each of $R^3$, $R^4$, $R^5$ is independently selected from C1-C4 alkyl, the resulting silicon-oxygen compound may be a hexaalkyl disiloxane. The resulting silicate typically corresponds to the cation included in the alkaline condition. For example, when the alkaline condition includes $Na^+$, the aforementioned silicate may be sodium silicate, and the phenyl silicate or alkyl silicate may be sodium phenyl silicate or sodium alkyl silicate. Further, the alkaline conditions can be provided by a suitable alkaline compound, which may be a suitable sodium salt (e.g., sodium hydroxide, sodium carbonate, sodium bicarbonate, etc.), so that alkaline conditions including $Na^+$ can be provided.

In the above method for preparation of the silicon-oxygen compound, the amount of the alkaline compound is substantially equal to or in excess of that of silyl ether polymer, so as to ensure the conversion rate of the reaction and to enable the reaction to be carried out in a sufficiently positive direction. For example, in the above method for preparation of the silicon-oxygen compound, the equivalence ratio of the silyl ether polymer to the alkaline compound may be 1:(0.5-5), 1:(0.5-0.6), 1:(0.6-0.7), 1:(0.7-0.8), 1: (0.8-0.9), 1:(0.9-1), 1: (1-1.1), 1:(1.1-1.2), 1: (1.2-1.5), 1:(1.5-2), 1:(2-3), 1:(3-4), or 1:(4-5).

In the above method for preparation of the silicon-oxygen compound, the reaction may be carried out at a temperature from room temperature to the boiling point of the solvent. In general, the temperature can be adjusted appropriately according to the reaction pressure of the reaction system in order to obtain a faster rate of reaction. For example, in the above method for preparation of the silicon-oxygen compound, the temperature may be 100 to 150° C., 100 to 105° C., 105 to 110° C., 110 to 120° C., 120 to 130° C., 130 to 140° C., or 140 to 150° C. In an embodiment, the reaction pressure may be atmospheric or no greater than 5 bar. The person skilled in the art may adjust the reaction time according to the reaction process. For example, in the above method for preparation of the silicon-oxygen compound, the reaction process may be monitored by TLC, chromatography, and other methods. In an embodiment, in the above method for preparation of the silicon-oxygen compound, the reaction time may be 0.5 to 10 h, 0.5 to 1 h, 1 to 2 h, 2 to 4 h, 4 to 6 h, or 6 to 10 h.

In the above method for preparation of the silicon-oxygen compound, a person skilled in the art may select a suitable method for post-treatment of the product obtained from the reaction, for example, by contacting the solid phase material with an aqueous solution of the alkaline compound sufficiently to provide an aqueous solution of the silicon-oxygen compound.

A second aspect of the present invention provides a method for preparation of 2-(chloromethyl)-5-(trifluoromethyl)-1,3,4-oxadiazole, comprising: performing a cyclization reaction on 1-(chloroacetyl)-2-(trifluoroacetyl)hydrazine in presence of a silicon compound and an acylamide compound to provide 2-(chloromethyl)-5-(trifluoromethyl)-1,3,4-oxadiazole, where the reaction equation is as follows:

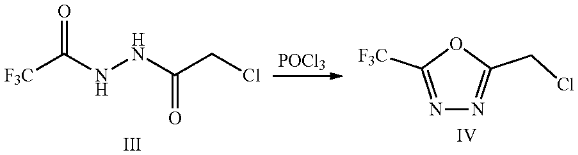

III IV the silicon compound is selected from one or more of compounds having a chemical structural formula shown below:

V

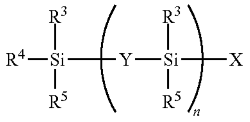

where $R^3$, $R^4$ and $R^5$ are each independently selected from H, Ph, C1-C4 alkyl, Cl, and Br, Y is O or is not present, n is selected from 0, 1, 2, 3, 4, and 5, and X is selected from Cl and Br.

In some embodiments of the present invention, for the silicon compound of formula V, each of $R^3$, $R^4$, and $R^5$ is independently selected from H, C1-C2 alkyl, Cl, and Br.

In another embodiment of the present invention, for the silicon compound of formula V, n is selected from 0 and 1.

In another embodiment of the present invention, for the silicon compound of formula V, X is selected from Cl and Br.

In another embodiment of the present invention, the silicon compound is selected from one or more of methyltrichlorosilane, dichlorodiethylsilane, dichlorodimethylsilane, trimethylchlorosilane, 1,1,2,2-tetrachloro-1,2-dimethyldisilane, silicon tetrachloride, dibromo(dimethyl)silane, bromotrimethylsilane, and 1,3-dichloro-1,1,3,3-tetramethyldisiloxane.

In the above cyclization reaction, the amount of the silicon compound can be suitably adjusted with respect to the compound of formula III, so as to ensure the conversion rate of the reaction and to enable the reaction to be carried out in a sufficiently positive direction. For example, in the above-mentioned cyclization reaction, the molar ratio of the compound of formula III to the silicon compound may be 1:(0.5-2.0), 1:(0.5-0.6), 1:(0.6-0.7), 1:(0.7-0.8), 1: (0.8-0.9), 1:(0.9-1.0), 1: (1.0-1.1), 1:(1.1-1.2), 1: (1.2-1.3), 1:(1.3-1.4), 1:(1.4-1.5), 1:(1.5-1.6), 1:(1.6-1.7), 1: (1.7-1.8), 1: (1.8-1.9), or 1:(1.9-2.0).

In the above cyclization reaction, the acylamide compound usually serves as a cyclization reagent and has a chemical structural formula of $RCONR^1R^2$; R is selected from hydrogen, saturated or unsaturated C1 to C8 aliphatic groups, and substituted or unsubstituted phenyl; $R^1$ and $R^2$ are each independently selected from saturated or unsaturated C1 to C8 aliphatic groups and phenyl, or, R and $R^1$, or R and $R^2$ together with their attached atoms form a five- or six-membered heterocyclic group. For instance, the acylamide compound is selected from one or more of N,N-dimethylformamide, N,N-diethylformamide, N,N-dimethylacetamide, N,N-diethylacetamide, N,N-diethylpropionamide, N,N-dimethylpropionamide, N,N-diphenylformamide, N,N-diphenylacetamide, N-methylpyrrolidone, and 1,3-dimethyl-2-imidazolidinone. The amount of the acylamide compound can be suitably adjusted with respect to the compound of formula III, so as to ensure the conversion of the reaction and to enable the reaction to be carried out in a sufficiently positive direction. For example, in the above-mentioned cyclization reaction, the molar ratio of the compound of formula III to the acylamide compound may be 1:(0.1-1.5), 1:(0.1-0.2), 1:(0.2-0.3), 1:(0.3-0.4), 1: (0.4-0.5), 1:(0.5-0.6), 1: (0.6-0.7), 1:(0.7-0.8), 1:(0.8-0.9), 1:(0.9-1.0), 1:(1.0-1.1), 1:(1.1-1.2), 1:(1.2-1.3), 1:(1.3-1.4), or 1:(1.4-1.5).

The above cyclization reaction is usually carried out in the presence of a solvent, and the solvent is usually a nonprotonic solvent and may be conducive to the reaction system. The type and amount of suitable solvents may be suitably adjusted by those skilled in the art. For example, in the above-mentioned cyclization reaction, the solvent may be selected from aromatic hydrocarbon solvents, etc. In an embodiment of the present invention, the solvent in the above-mentioned cyclization reaction may be selected from one or more of benzene, toluene, dimethylbenzene, trimethylbenzene, chlorobenzene, dichlorobenzene, trichlorobenzene, etc. In an embodiment, in the above cyclization reaction, the weight of the solvent may be 1 to 8 times, 1 to 2 times, 2 to 4 times, or 4 to 8 times the weight of the reaction substrate.

In the above-mentioned cyclization reaction, the reaction may be carried out at a temperature ranging from room temperature to the boiling point of the solvent, and preferably under heated conditions. For example, in the above cyclization reaction, the temperature may be 70 to 150° C., 70 to 80° C., 80 to 90° C., 90 to 100° C., 100 to 110° C., 110 to 120° C., 120 to 130° C., 130 to 140° C., or 140 to 150° C. The person skilled in the art may adjust the reaction time according to the reaction process. For example, in the above-mentioned cyclization reaction, the reaction process may be monitored by TLC, chromatography, and other methods. In an embodiment, in the above cyclization reaction, the reaction time may be 1 to 20 h, 1 to 2 h, 2 to 4 h, 4 to 6 h, 6 to 8 h, 8 to 12 h, or 12 to 20 h.

In the above cyclization reaction, the person skilled in the art may select a suitable method for the post-treatment of the reaction product, which may include, for example, quenching with water, adjusting pH of the system, performing solid-liquid separation, and removing organic solvent, so as to provide 2-(chloromethyl)-5-(trifluoromethyl)-1,3,4-oxadiazole. After the reaction, the system is quenched with water, the pH of the system is adjusted accordingly (e.g., adjusting the pH to be within a range from weakly acidic to weakly alkaline, more specifically it can be pH=6-8), the solid and liquid phases are separated, and the solvent is removed from the organic phase of the resulting liquid phase to yield 2-(chloromethyl)-5-(trifluoromethyl)-1,3,4-oxadiazole. The obtained 2-(chloromethyl)-5-(trifluoromethyl)-1,3,4-oxadiazole may be further purified to provide a product with higher purity. Suitable purification methods (such as distillation) are known to those skilled in the art.

The method for preparation of 2-(chloromethyl)-5-(trifluoromethyl)-1,3,4-oxadiazole provided by the present invention may further comprise: performing a reaction on the solid phase substance (obtained from the solid-liquid separation) under an alkaline condition to provide a silicon-oxygen compound. The above-mentioned solid phase substance includes mainly the silyl ether polymer produced during the cyclization reaction for the preparation of 2-(chloromethyl)-5-(trifluoromethyl)-1,3,4-oxadiazole, which can be hydrolyzed into a corresponding silicon-oxygen compound under alkaline conditions.

In the above method for preparation of the silicon-oxygen compound, the silicon-oxygen compound varies depending on the substituents of the silicon compounds used in the cyclization reaction. For example, when $R^3$, $R^4$, and $R^5$ are each independently selected from Cl and Br, the resulting silicon-oxygen compound may be a silicate; when one of $R^3$, $R^4$, and $R^5$ is selected from Ph or C1-C4 alkyl and the remaining two are each independently selected from Cl and Br, the resulting silicon-oxygen compound may be a phenyl silicate or an alkyl silicate; when two of $R^3$, $R^4$, $R^5$ are each independently selected from C1-C4 alkyl and the remaining one is selected from Cl and Br, the resulting silicon-oxygen compound may be a polydialkylsiloxane; when each of $R^3$, $R^4$, $R^5$ is independently selected from C1-C4 alkyl, the resulting silicon-oxygen compound may be a hexaalkyl disiloxane. The resulting silicate typically corresponds to the cation included in the alkaline condition. For example, when the alkaline condition includes $Na^+$, the aforementioned silicate may be sodium silicate, and the phenyl silicate or alkyl silicate may be sodium phenyl silicate or sodium alkyl silicate. In an embodiment, the alkaline conditions can be provided by a suitable alkaline compound, which may be a suitable sodium salt (e.g., sodium hydroxide, sodium carbonate, sodium bicarbonate, etc.), so that alkaline conditions including $Na^+$ can be provided.

In the above method for preparation of the silicon-oxygen compound, the amount of the alkaline compound is substantially equal to or in excess of that of silyl ether polymer, so as to ensure the conversion rate of the reaction and to enable the reaction to be carried out in a sufficiently positive direction. For example, in the above method for preparation of the silicon-oxygen compound, the equivalence ratio of the silyl ether polymer to the alkaline compound may be 1:(0.5-5), 1:(0.5-0.6), 1:(0.6-0.7), 1:(0.7-0.8), 1: (0.8-0.9), 1:(0.9-1), 1: (1-1.1), 1:(1.1-1.2), 1: (1.2-1.5), 1:(1.5-2), 1:(2-3), 1:(3-4), or 1:(4-5).

In the above method for preparation of the silicon-oxygen compound, the reaction may be carried out at a temperature ranging from room temperature to the boiling point of the solvent. In general, the temperature can be adjusted appropriately according to the reaction pressure of the reaction system in order to obtain a faster rate of reaction.

For example, in the above method for preparation of the silicon-oxygen compound, the temperature may be 100 to 150° C., 100 to 105° C., 105 to 110° C., 110 to 120° C., 120 to 130° C., 130 to 140° C., or 140 to 150° C. In an embodiment, the reaction pressure may be atmospheric or no greater than 5 bar. The person skilled in the art may adjust the reaction time according to the reaction process. For example, in the above method for preparation of the silicon-oxygen compound, the reaction process may be monitored by TLC, chromatography, and other methods. In an embodiment, in the above method for preparation of the silicon-oxygen compound, the reaction time may be 0.5 to 10 h, 0.5 to 1 h, 1 to 2 h, 2 to 4 h, 4 to 6 h, or 6 to 10 h.

In the above method for preparation of the silicon-oxygen compound, a person skilled in the art may select a suitable method for post-treatment of the product obtained from the reaction, for example, by contacting the solid phase material with an aqueous solution of the alkaline compound sufficiently to provide an aqueous solution of the silicon-oxygen compound. The present invention provides a use of a silicon compound in cycloaddition reactions, and further provides a method for preparation of 2-chloro-5-chloromethylpyridine and 2-(chloromethyl)-5-(trifluoromethyl)-1,3,4-oxadiazole. The silicon compounds or/and acylamide compound provided by the present invention serve as cyclization reagents, and compared with the existing technology, the method of the present disclosure has several advantages. It produces a high yield of cyclization, generates less waste, and is environmentally friendly.

Additionally, the by-products can be recycled. This method is economically beneficial, easy to operate, and well-suited for industrial production. Overall, it has great potential for industrialization.

The invention of this application is further described below by means of embodiments; however, the scope of this application is not limited thereto.

Embodiment 1

Preparation of 2-chloro-5-chloromethylpyridine 1-1

270 g of toluene, 90 g of 4,5-dichloro-4-methoxypentanenitrile, and 18.3 g of N,N-dimethylformamide (DMF) were added to a glass reaction flask, the internal temperature was raised to 100-110° C., 89.7 g of methyltrichlorosilane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 68.9 g of 2-chloro-5-chloromethylpyridine was obtained with a purity of 99.7% (GC) and a yield rate of 85%.

1-2

270 g of toluene, 90 g of 4,5-dichloro-4-methoxypentanenitrile, and 18.3 g of N,N-dimethylformamide (DMF) were added to a glass reaction flask, the internal temperature was raised to 100-110° C., 117.8 g of dichlorodiethylsilane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 68.9 g of 2-chloro-5-chloromethylpyridine was obtained with a purity of 99.2% (GC) and a yield rate of 85%.

1-3

360 g of chlorobenzene, 90 g of 4,5-dichloro-4-methoxypentanenitrile, and 39.2 g of N,N-dimethylacetamide (DMAC) were added to a glass reaction flask, the internal temperature was raised to 120~130° C., 116.2 g of dichlorodimethylsilane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 72.9 g of 2-chloro-5-chloromethylpyridine was obtained with a purity of 99.5% (GC) and a yield rate of 90%.

1-4

270 g of toluene, 90 g of 4,5-dichloro-4-methoxypentanenitrile, and 44.6 g of N-methylpyrrolidone (NMP) were added to a glass reaction flask, the internal temperature was raised to 100-110° C., 103.2 g of trimethylchlorosilane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 65.6 g of 2-chloro-5-chloromethylpyridine was obtained with a purity of 99.3% (GC) and a yield rate of 81%.

1-5

270 g of toluene, 90 g of 4,5-dichloro-4-methoxypentanenitrile, and 18.3 g of N,N-dimethylformamide (DMF) were added to a glass reaction flask, the internal temperature was raised to 100-110° C., 148.2 g of 1,1,2,2-tetrachloro-1,2-dimethyldisilane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 66.4 g of 2-chloro-5-chloromethylpyridine was obtained with a purity of 99.5% (GC) and a yield rate of 82%.

1-6

270 g of toluene, 90 g of 4,5-dichloro-4-methoxypentanenitrile, and 21.9 g of N,N-dimethylformamide (DMF) were added to a glass reaction flask, the internal temperature was raised to 100-110° C., 110.4 g of silicon tetrachloride was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 65.6 g of 2-chloro-5-chloromethylpyridine was obtained with a purity of 99.5% (GC) and a yield rate of 81%.

1-7

270 g of toluene, 90 g of 4,5-dichloro-4-methoxypentanenitrile, and 11 g of N,N-dimethylformamide (DMF) were added to a glass reaction flask, the internal temperature was raised to 100-110° C., 163.5 g of dibromo(dimethyl)silane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 67.2 g of 2-chloro-5-chloromethylpyridine was obtained with a purity of 99.5% (GC) and a yield rate of 83%.

1-8

270 g of toluene, 90 g of 4,5-dichloro-4-methoxypentanenitrile, and 34.7 g of N-methylpyrrolidone (NMP) were added to a glass reaction flask, the internal temperature was raised to 100-110° C., 153.1 g of bromotrimethylsilane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 64 g of 2-chloro-5-chloromethylpyridine was obtained with a purity of 99.5% (GC) and a yield rate of 79%.

1-9

270 g of toluene, 90 g of 4,5-dichloro-4-methoxypentanenitrile, and 25.6 g of N,N-dimethylformamide (DMF) were added to a glass reaction flask, the internal temperature was raised to 100-110° C., 182.9 g of 1,3-dichloro-1,1,3,3-tetramethyldisiloxane was added dropwise under reflux, and the system was then refluxed for 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 64.8 g of 2-chloro-5-chloromethylpyridine was obtained with a purity of 99.6% (GC) and a yield rate of 80%.

1-10

200 g of toluene and 18.3 g of N,N-dimethylformamide (DMF) were added into a glass reaction flask, and the internal temperature was raised to 100-110° C. The following two reactants were prepared: one was reactant A, 117.8 g of dichlorodiethylsilane, and the other one was reactant B, 90 g of 4,5-dichloro-4-methoxypentanenitrile and 120 g of toluene. Reactants A and B were added dropwise simultaneously under reflux. Afterward, the system was refluxed for another 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 70.5 g of 2-chloro-5-chloromethylpyridine was obtained with a purity of 99.3% (GC) and a yield rate of 87%.

Embodiment 2

Preparation of 2-(chloromethyl)-5-(trifluoromethyl)-1,3,4-oxadiazole 2-1

360 g of toluene, 102.3 g of 1-(chloroacetyl)-2-(trifluoroacetyl)hydrazine, and 18.3 g of N,N-dimethylformamide (DMF) were added into a glass reaction flask, the internal temperature was raised to 100-110° C., and 97.1 g of methyltrichlorosilane was added dropwise under reflux. Afterward, the system was refluxed for another 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 75.5 g of 2-(chloromethyl)-5-(trifluoromethyl)-1,3,4-oxadiazole was obtained with a purity of 99.2% (GC) and a yield rate of 81%.

2-2

400 g of chlorobenzene, 102.3 g of 1-(chloroacetyl)-2-(trifluoroacetyl)hydrazine, and 39.2 g of N,N-dimethylacetamide (DMAC) were added into a glass reaction flask, the internal temperature was raised to 120~130° C., and 116.2 g of dichlorodimethylsilane was added dropwise under reflux. Afterward, the system was refluxed for another 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 82.1 g of 2-(chloromethyl)-5-(trifluoromethyl)-1,3,4-oxadiazole was obtained with a purity of 99.5% (GC) and a yield rate of 88%.

2-3

360 g of toluene, 102.3 g of 1-(chloroacetyl)-2-(trifluoroacetyl)hydrazine, and 44.6 g of N-methylpyrrolidone (NMP) were added into a glass reaction flask, the internal temperature was raised to 100-110° C., and 108.6 g of trimethylchlorosilane was added dropwise under reflux. Afterward, the system was refluxed for another 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 79.3 g of 2-(chloromethyl)-5-(trifluoromethyl)-1,3,4-oxadiazole was obtained with a purity of 99.6% (GC) and a yield rate of 85%.

2-4

400 g of toluene, 102.3 g of 1-(chloroacetyl)-2-(trifluoroacetyl)hydrazine, and 14.6 g of N,N-dimethylformamide (DMF) were added into a glass reaction flask, the internal temperature was raised to 100-110° C., and 163.5 g of dibromo(dimethyl)silane was added dropwise under reflux. Afterward, the system was refluxed for another 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 76.5 g of 2-(chloromethyl)-5-(trifluoromethyl)-1,3,4-oxadiazole was obtained with a purity of 99.2% (GC) and a yield rate of 82%.

2-5

200 g of chlorobenzene and 18.3 g of N,N-dimethylformamide (DMF) were added into a glass reaction flask, and the internal temperature was raised to 100-110° C. The following two reactants were prepared: one was reactant A, 97.1 g of methyltrichlorosilane, and the other one was reactant B, 102.3 g of 1-(chloroacetyl)-2-(trifluoroacetyl) hydrazine and 120 g of chlorobenzene. Reactants A and B were added dropwise simultaneously under reflux. Afterward, the system was refluxed for another 2 hours. The temperature was lowered to 60° C., 10 g of water was added, the temperature was again lowered to 20~30° C., and 15 g of 30% NaOH aqueous solution was added dropwise. The pH of the reaction system was adjusted to about 6-7, and the reaction system was filtered. The resulting filter cake was rinsed with 50 g of toluene to obtain an organic phase, and the solvent in the organic phase was removed. 78.3 g of 2-(chloromethyl)-5-(trifluoromethyl)-1,3,4-oxadiazole was obtained with a purity of 99.7% (GC) and a yield rate of 84%.

Embodiment 3

Preparation of Aqueous Sodium Alkyl Silicate Solution 3-1

150 g of tap water was added into a stainless steel autoclave, and 100 g of the silicon polymer obtained from the above filtration in Example 1-1 was added under stirring. 120 g of 30% aqueous sodium hydroxide was quickly added, accompanied by an exotherm, the system was heated to reflux, and refluxed for another 4 hours until no solid phase was present. The internal temperature was lowered to 40-50° C., the reaction system was filtered to obtain 365 g of a clear and colorless aqueous solution of sodium methylsiliconate.

3-2

150 g of tap water was added into a stainless steel autoclave, and 100 g of the silicon polymer obtained from the above filtration in Example 1-6 was added under stirring. 130 g of 30% aqueous sodium hydroxide was quickly added, accompanied by an exotherm, the system was heated to reflux, and refluxed for another 4 hours until no solid phase was present. The internal temperature was lowered to 40-50° C., the reaction system was filtered to obtain 376 g of a clear and colorless aqueous solution of sodium silicate. The $SiO_2$ content of the water glass is 28.09%, the $Na_2O$ content of the water glass is 8.87%, and the water glass module is 3.27%.

3-3

150 g of tap water was added into a stainless steel autoclave, and 100 g of the silicon polymer obtained from the above filtration in Example 1-3 was added under stirring. 8 g of hydroxylamine hydrochloride was added to serve as a catalyst, and 100 g of 30% aqueous sodium hydroxide was quickly added, accompanied by an exotherm.

The system was heated to reach an internal temperature of 120° C., at which time the pressure in the stainless steel autoclave was approximately 1.5 bar, and the system was held at 120° C. for 2 hours until no solid phase was present. The internal temperature was lowered to 40-50° C., the reaction system was filtered to obtain 344 g of a clear and colorless aqueous solution of polydimethylsiloxane.

3-4

150 g of tap water was added into a stainless steel autoclave, and 100 g of the silicon polymer obtained from the above filtration in Example 2-2 was added under stirring. 100 g of 30% aqueous sodium hydroxide was quickly added, accompanied by an exotherm, the internal temperature of the stainless steel autoclave was raised to 145° C., the pressure inside the stainless steel autoclave was about 2.5 bar, and the reaction time was 1 h after the stainless steel autoclave was sealed. The internal temperature was then lowered to 40-50° C., and the reaction system was filtered to obtain 346 g of a clear and colorless aqueous solution of polydimethylsiloxane.

Control Example 1

Preparation of 2-chloro-5-chloromethylpyridine 0.1 mol of compound CCC was dissolved in 20 ml of toluene and 2.19 g of N,N-dimethylformamide (0.03 mol) was added. The system was heated to 90° C. in an oil bath, and 6.15 g (0.04 mol) of phosphorus oxychloride was added dropwise. The temperature of the system was maintained between 90-95° C., phosphorus oxychloride was added dropwise for 2 h, and then the system was maintained at 95° C. for 30 minutes. The system was cooled to 50° C., 10 ml of water was added, and then 10.7 g of 30% NaOH aqueous solution was added dropwise at 20-50° C. until the pH was about 8.0-10.0. The system was stratified until an upper layer of toluene was shown, the solvent was then removed, and 14.1 g of brown solid was obtained with a CCMP of 71.6% and a yield rate of 62.3%, where CCMP was measured by the GC internal standard detection method.

In summary, the present invention effectively overcomes the shortcomings of the prior art and has high industrial value.

The above embodiments are only illustrative of the principle and efficacy of the present invention, and are not intended to limit the present invention. Any person skilled in the art may modify or change the above embodiments without violating the spirit and scope of the present invention. Therefore, all equivalent modifications or alterations made by a person having ordinary knowledge in the art, without departing from the spirit and technical ideas disclosed in the present invention, shall still be covered by the claims of the present invention.

What is claimed is:

1. A method for preparation of 4,5-dichloro-4-methoxypentanenitrile, comprising: performing a cyclization reaction on 4,5-dichloro-4-methoxypentanenitrile in presence of a silicon compound and an acylamide compound to provide 2-chloro-5-chloromethylpyridine, wherein a reaction equation of the cycllization reaction is as follows:

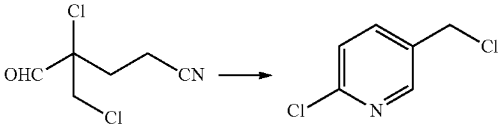

I

II wherein the silicon compound is selected from one or more of compounds having a chemical structural formula shown below:

V

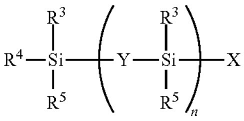

wherein $R^3$, $R^4$, and $R^5$ are each independently selected from H, Ph, C1-C4 alkyl, Cl, and Br, Y is O or is not present, n is selected from 0, 1, 2, 3, 4, and 5, and X is selected from Cl and Br.

2. The method for preparation of 2-chloro-5-chloromethylpyridine of claim 1, wherein in the compound of formula V, $R^3$, $R^4$, and $R^5$ are each independently selected from H, Ph, C1-C2 alkyl, Cl, and Br, n is selected from 0 and 1, and X is selected from Cl and Br.

3. The method for preparation of 2-chloro-5-chloromethylpyridine of claim 1, wherein the silicon compound is selected from one or more of methyltrichlorosilane, dichlorodiethylsilane, dichlorodimethylsilane, trimethylchlorosilane, 1,1,2,2-tetrachloro-1,2-dimethyldisilane, silicon tetrachloride, dibromo (dimethyl) silane, bromotrimethylsilane, and 1,3-dichloro-1,1,3,3-tetramethyldisiloxane.

4. The method for preparation of 2-chloro-5-chloromethylpyridine of claim 1, wherein the acylamide compound has a chemical structural formula shown as $RCONR^1R^2$, wherein R is selected from hydrogen, saturated or unsaturated C1 to C8 aliphatic groups, and substituted or unsubstituted phenyl, $R^1$ and $R^2$ are each independently selected from saturated or unsaturated C1 to C8 aliphatic groups and phenyl, or R and $R^1$, or R and $R^2$ together with their attached atoms form a five- or six-membered heterocyclic group, and/or, in the cyclization reaction, a molar ratio of the compound of formula I to the acylamide compound is 1: (0.1-1.5);

and/or, the cyclization reaction is carried out in the presence of a solvent, wherein the solvent is a nonprotonic solvent;

and/or, the cyclization reaction is carried out at a temperature of 70 to 150° C.;

and/or, in the cyclization reaction, a molar ratio of the compound of formula I to the silicon compound is 1: (0.5-2.0);

and/or, a post-treatment of the cyclization reaction comprises: quenching with water, adjusting pH of reaction system, performing solid-liquid separation, and removing organic solvent.

5. The method for preparation of 2-chloro-5-chloromethylpyridine of claim 4, further comprising: performing a reaction on a solid phase substance under an alkaline condition to obtain a silicon-oxygen compound.

6. A method for preparation of 2-(chloromethyl)-5-(trifluoromethyl)-1,3,4-oxadiazole, comprising: performing a cyclization reaction on 1-(chloroacetyl)-2-(trifluoroacetyl) hydrazine in presence of a silicon compound and an acylamide compound to provide 2-(chloromethyl)-5-(trifluoromethyl)-1,3,4-oxadiazole, wherein a reaction equation of the cyclization reaction is as follows:

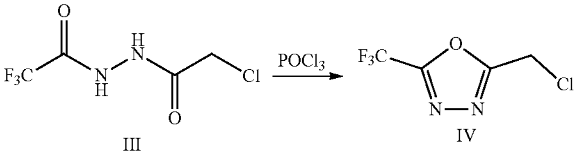

III

IV wherein the silicon compound is selected from one or more of compounds having a chemical structural formula shown below:

V

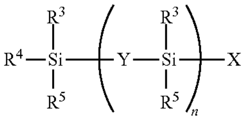

wherein $R^3$, $R^4$, and $R^5$ are each independently selected from H, Ph, C1-C4 alkyl, Cl, and Br, Y is O or is not present, n is selected from 0, 1, 2, 3, 4, and 5, and X is selected from Cl and Br.

7. The method for preparation of 2-(chloromethyl)-5-(trifluoromethyl)-1,3,4-oxadiazole of claim 6, wherein in the compound of formula V, $R^3$, $R^4$, and $R^5$ are each independently selected from H, C1-C2 alkyl, Cl, and Br, n is selected from 0 and 1, and X is selected from Cl and Br.

8. The method for preparation of 2-(chloromethyl)-5-(trifluoromethyl)-1,3,4-oxadiazole of claim 6, wherein the silicon compound is selected from one or more of methyltrichlorosilane, dichlorodiethylsilane, dichlorodimethylsilane, trimethylchlorosilane, 1, 1,2,2-tetrachloro-1,2-dimethyldisilane, silicon tetrachloride, dibromo (dimethyl) silane, bromotrimethylsilane, and 1,3-dichloro-1,1,3,3-tetramethyldisiloxane.

9. The method for preparation of 2-(chloromethyl)-5-(trifluoromethyl)-1,3,4-oxadiazole of claim 1, wherein the acylamide compound has a chemical structural formula shown as $RCONR^1R^2$, wherein R is selected from hydrogen, saturated or unsaturated C1 to C8 aliphatic groups, and substituted or unsubstituted phenyl, $R^1$ and $R^2$ are each independently selected from saturated or unsaturated C1 to C8 aliphatic groups and phenyl, or R and $R^1$, or R and $R^2$ together with their attached atoms form a five- or six-membered heterocyclic group, and/or, in the cyclization reaction, a molar ratio of the compound of formula III to the acylamide compound is 1: (0.1-1.5);

and/or, the cyclization reaction is carried out in the presence of a solvent, wherein the solvent is a nonprotonic solvent;

and/or, the cyclization reaction is carried out at a temperature of 70 to 150° C.;

and/or, in the cyclization reaction, a molar ratio of the compound of formula III to the silicon compound is 1:(0.5-2.0);

and/or, a post-treatment of the cyclization reaction comprises: quenching with water, adjusting pH of reaction system, performing solid-liquid separation, and removing organic solvent.

10. The method for preparation of 2-(chloromethyl)-5-(trifluoromethyl)-1,3,4-oxadiazole of claim 9, further comprising: performing a reaction on a solid phase substance under an alkaline condition to obtain a silicon-oxygen compound.

11. The method for preparation of 2-chloro-5-chloromethylpyridine of claim 4, wherein the acylamide compound is selected from one or more of N,N-dimethylformamide, N,N-diethylformamide, N,N-dimethylacetamide, N,N-diethylacetamide, N,N-diethylpropionamide, N,N-dimethylpropionamide, N,N-diphenylformamide, N,N-diphenylacetamide, N-methylpyrrolidone, and 1,3-dimethyl-2-imidazolidinone;

and/or, the solvent is an aromatic hydrocarbon solvent.

12. The method for preparation of 2-chloro-5-chloromethylpyridine of claim 5, wherein the silicon-oxygen compound is selected from silicates.

13. The method for preparation of 2-(chloromethyl)-5-(trifluoromethyl)-1,3,4-oxadiazole of claim 9, wherein the acylamide compound is selected from one or more of N,N-dimethylformamide, N,N-diethylformamide, N,N-dimethylacetamide, N,N-diethylacetamide, N,N-diethylpropionamide, N,N-dimethylpropionamide, N,N-diphenylformamide, N,N-diphenylacetamide, N-methylpyrrolidone, and 1,3-dimethyl-2-imidazolidinone;

and/or, the solvent is an aromatic hydrocarbon solvent.

14. The method for preparation of 2-(chloromethyl)-5-(trifluoromethyl)-1,3,4-oxadiazole of claim 10, wherein the silicon-oxygen compound is selected from silicates.

* * * * *